United States Patent [19]

Reap

[11] 4,191,553
[45] Mar. 4, 1980

[54] HERBICIDAL SULFAMATES

[75] Inventor: James J. Reap, Wilmington, Del.

[73] Assignee: E. I. Du Pont de Nemours and Company, Wilmington, Del.

[21] Appl. No.: 882,918

[22] Filed: Mar. 2, 1978

[51] Int. Cl.$^2$ .................................................. A01N 9/22
[52] U.S. Cl. ........................................... 71/92; 71/93; 544/211; 544/321; 544/332
[58] Field of Search .................. 544/211, 321, 332; 71/92, 93

[56] References Cited

U.S. PATENT DOCUMENTS

| | | | |
|---|---|---|---|
| 3,939,158 | 2/1976 | Begrich | 544/211 X |
| 4,120,691 | 10/1978 | Levitt | 71/93 |
| 4,127,405 | 11/1978 | Levitt | 544/211 X |

FOREIGN PATENT DOCUMENTS

| | | |
|---|---|---|
| 940292 | 3/1956 | Fed. Rep. of Germany . |
| 1468747 | 1/1967 | France . |
| 121788 | 9/1966 | Netherlands . |

OTHER PUBLICATIONS

Lohaus, Chem. Ber., 105 (1972), pp. 2791–2799.
Logemann, et al., C.A., 53 (1959), 18052–18053.
Wojciechowski, C.A., 59 (1963), 1633.

*Primary Examiner*—Joseph Paul Brust

[57] ABSTRACT

N-(heterocyclicaminocarbonyl) arylsulfamates, such as phenyl[(4,6-dimethoxypyrimidin-2-yl)-aminocarbonyl]-sulfamate or 2-chlorophenyl[(4-methoxy-6-methyl-pyrimidin-2-yl)-aminocarbonyl]sulfamate, are useful for plant growth retardation, brush control and weed control in crops.

48 Claims, No Drawings

HERBICIDAL SULFAMATES

BACKGROUND OF THE INVENTION

This invention relates to N-(heterocyclicaminocarbonyl)arylsulfamate agricultural chemicals.

*Chem. Ber.*, 105, 2791 (1972) describes the preparation of N-butylcarbamoyl-p-toluenesulfamate, but does not claim utility as a pesticide:

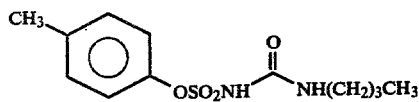

German Pat. No. 940,292 describes the preparation of N-[arylcarbamoyl]arylsulfamides and claims utility as textile assistants, pharmaceuticals and pesticides:

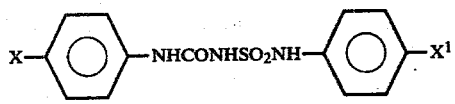

wherein each of X and X¹ is H, or each is ethoxy.

Netherlands Pat. No. 121,788, published Sept. 15, 1966, teaches the preparation of the following compounds and their use as general or selective herbicides:

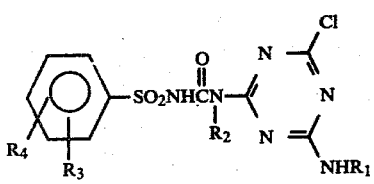

wherein
R₁ and R₂ may independently be alkyl of 1–4 carbon atoms; and
R₃ and R₄ may independently be hydrogen, chlorine or alkyl of 1–4 carbon atoms.

French Pat. No. 1,468,747 discloses para-substituted phenylsulfonamides, useful as antidiabetic agents:

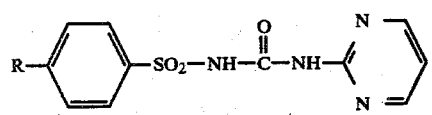

wherein R=H, halogen, CF₃ or alkyl.

Logemann et al. Chem. Ab., 53, 18052 g (1959), disclose a number of sulfonamides, including uracil derivatives and those having the formula:

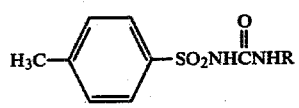

wherein R is butyl, phenyl or

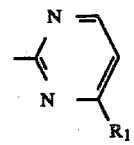

and R₁ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

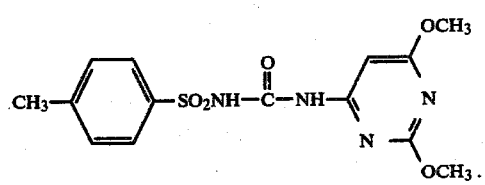

Based upon similarity to a known compound, the author predicted hypoglycemic activity for the foregoing compound.

The presence of undesired vegetation causes substantial damage to useful crops, especially agricultural products that satisfy man's basic food and fiber needs, such as cotton, rice, corn, wheat, soybean and the like. The current population explosion and concomitant world food and fiber shortage demand improvements in the efficiency of producing these crops. Preventing or minimizing the loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. However, the need exists for still more effective herbicides that destroy or control weeds without causing significant damage to useful crops.

SUMMARY OF THE INVENTION

According to this invention, there are provided novel compounds of Formula I and their agriculturally suitable salts, suitable agricultural compositions containing them, and methods of using them as general herbicides having both preemergence and postemergence activity:

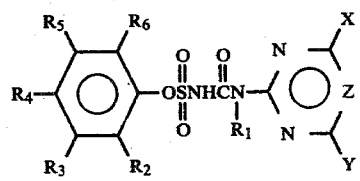

wherein
$R_1$ is H, OCH₃ or alkyl of 1–3 carbons;
$R_2$ is H, Cl, F, Br, NO₂, alkyl of 1–4 carbons, alkoxy of 1–4 carbons, CF₃ or $$\overset{O}{\underset{\|}{-CR_7}};$$

$R_3$ is H, Cl, F, Br, $CH_3$, or alkoxy of 1–4 carbons;
$R_4$ is H, Cl, F, Br, $NO_2$, alkyl of 1–4 carbons, alkoxy of 1–4 carbons, CN or $$\overset{O}{\underset{\|}{-CR_7}};$$

$R_5$ is H, Cl, F, Br, $CH_3$, $NO_2$ or $CF_3$;
$R_6$ is H, Cl, F, Br, alkyl of 1–4 carbons or alkoxy of 1–4 carbons;
$R_7$ is Na+O—, OH, or alkoxy of 1–4 carbons;
X is $CH_3$, $CH_3CH_2$, alkoxy of 1–3 carbons, $CH_3OCH_2$, $CH_3OCH_2CH_2O$, $CH_3S$, $CH_3CH_2S$, $CF_3$ or Cl;
Y is $CH_3$, $CH_3CH_2$, alkoxy of 1–3 carbons, $CH_3OCH_2$, $CH_3OCH_2CH_2O$, $CH_3S$ or $CH_3CH_2S$; and
Z is CH or N;
provided that
 only one of $R_2$, $R_3$ or $R_4$ is alkoxy; and
 when $R_5$ is $NO_2$, $R_4$ is other than $NO_2$.

Preferred for their high herbicidal activity and/or favorable cost are those compounds of Formula I wherein independently
$R_1$ is H; and
X and Y are independently $CH_3$ or $CH_3O$.

More preferred for their higher herbicidal activity and/or more favorable cost are those of the preferred compounds wherein
$R_2$ and $R_4$ are independently H, Cl, alkyl of 1–4 carbons, $CH_3O$ or $$\overset{O}{\underset{\|}{R_7C}};$$

$R_3$ is H, Cl, $CH_3$ or —$OCH_3$;
$R_5$ is H, Cl, $CH_3$ or $NO_2$;
$R_6$ is H, Cl, alkyl of 1–4 carbons or —$OCH_3$; and
$R_7$ is $CH_3O$, or $CH_3CH_2O$.

Most preferred for their even higher herbicidal activity and/or exceptionally favorable cost are those of the more preferred compounds wherein $R_3$, $R_4$ and $R_5$ are H.

Specifically preferred for their outstanding herbicidal activity and/or very highly favorable cost are
phenyl[(4,6-dimethoxypyrimidin-2-yl)-aminocarbonyl]-sulfamate, m.p. 136°–139° C.;
phenyl[(4,6-dimethoxy-1,3,5-triazin-2-yl)-aminocarbonyl]sulfamate, m.p. 160°–161° C.;
2-chlorophenyl[(4-methoxy-6-methylpyrimidin-2-yl)aminocarbonyl]sulfamate, m.p. 138°–141° C.
2,6-dichlorophenyl[(4-methoxy-6-methylpyrimidin-2-yl)-aminocarbonyl]sulfamate, m.p. 167°–169° C.
2,6-dimethoxyphenyl[(4-methoxy-6-methylpyrimidin-2-yl)-aminocarbonyl]sulfamate, m.p. 177°–179° C.
2,6-dimethylphenyl[(4-methoxy-6-methylpyrimidin-2-yl)-aminocarbonyl]sulfamate, m.p. 188°–190° C.
methyl 2-{N-[(4-methoxy-6-methylpyrimidin-2-yl)aminocarbonyl]aminosulfonyloxy}benzoate, m.p. 106°–110° C.;
2-nitrophenyl[(4,6-dimethoxypyrimidin-2-yl)aminocarbonyl]sulfamate, m.p. 153°–154° C.; and
methyl 2-{N-[(4,6-dimethoxypyrimidin-2-yl)aminocarbonyl]aminosulfonyloxy}-3-methylbenzoate, m.p. 137°–139° C.

Synthesis

As shown in Equation 1, the compounds of Formula I can be prepared by reacting an appropriately substituted aryloxysulfonyl isocyanate of Formula II with an appropriate 2-aminopyrimidine or 2-amino-1,3,5-triazine of Formula III; $R_1$ through $R_6$, X, Y and Z being as previously defined:

Equation 1.

$$\underset{(II)}{\text{Ar-OSO}_2\text{NCO}} + \underset{(III)}{\text{HN(R}_1\text{)-Het}} \longrightarrow$$

$$\underset{(I)}{\text{Ar-OSO}_2\text{NH-CO-N(R}_1\text{)-Het}}$$

(where Ar is the substituted phenyl bearing $R_2$–$R_6$ and Het is the pyrimidine/triazine bearing X, Y, Z)

The reaction is best carried out in inert aprotic organic solvents such as methylene chloride, tetrahydrofuran or acetonitrile, at ambient pressure and temperature. The mode of addition is not critical; however, it is often convenient to add the aryloxysulfonyl isocyanate II in solution to a stirred suspension of the amine III.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, hexanes, or ethyl ether, and filtration.

The intermediate aryloxysulfonyl isocyanates II can be prepared by reacting substituted phenols with chlorosulfonyl isocyanate and heating to reflux in a solvent such as toluene or xylene according to the procedure of Lohaus, Chem. Ber. 105, 2791 (1972). Chlorosulfonyl isocyanate is commercially available.

The synthesis of heterocyclic amine derivatives has been reviewed in "The Chemistry of Heterocyclic Compounds," a series published by Interscience Publ., New York and London. 2-Aminopyrimidines are described by D. J. Brown in "The Pyrimidines," Vol. XVI of the above series.

Agriculturally suitable salts of compounds of Formula I are also useful herbicides and can be prepared by a number of ways known to the art. For example, metal salts can be made by treating compounds of Formula I with a solution of an alkali or alkaline earth metal compound having a sufficiently basic anion (e.g., carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g. alkali metal or quaternary amine salt) with a solution containing the cation to be exchanged. That method is most effective when the desired salt containing the exchanged cation is insoluble in water and can be separated by filtration.

Exchange may also be effected by passing an aqueous solution of a salt of a compound of Formula I (e.g. an alkali metal or quaternary amine salt) through a column packed with a cation exchange resin containing the cation to be exchanged. In that method, the cation of the resin is exchanged for that of the original salt and the desired product is eluted from the column. That method is particularly useful when the desired salt is water soluble.

Acid addition salts, useful in this invention, can be obtained by reacting a compound of Formula I with a suitable acid, e.g. p-toluenesulfonic acid, trichloroacetic acid or the like.

The compounds of this invention and their preparation are further illustrated by the following examples wherein temperatures are given in degrees centigrade.

EXAMPLE I

Phenyl[(4,6-dimethoxypyrimidin-2-yl)-aminocarbonyl]-sulfamate

To a well stirred solution of 1.6 g of chlorosulfonyl isocyanate in 7 ml of dry xylene at ambient temperature and pressure was added 0.9 g of phenol. The resulting mixture was heated to reflux temperature for 1.5 hours. The solvent was removed under reduced pressure to give a clear oil. The oil was diluted with 5 ml of methylene chloride and added to a cooled (ice-water bath) suspension of 1.5 g of 2-amino-4,6-dimethoxypyrimidine in 10 ml of methylene chloride. The solvent was removed under vacuum. The resultant oil was triturated with 1-chlorobutane and filtered to yield 2.6 g of white solid, m.p. 136°–139° C. The infrared spectrum showed characteristic absorption bands at 3150 cm$^{-1}$, 1720 cm$^{-1}$, 1625 cm$^{-1}$, 1580 cm$^{-1}$.

EXAMPLE 2

2-Bromophenyl[(4,6-dimethoxypyrimidin-2-yl)-aminocarbonyl]sulfamate

To a well stirred solution of 1.6 g of chlorosulfonyl isocyanate in 7 ml of dry xylene at ambient temperature and pressure was added 1.73 g of 2-bromophenol. The resulting mixture was heated to reflux temperature for 2 hours. The solvent was removed under reduced pressure to give a clear oil. The oil was diluted with 5 ml of methylene chloride and added to a suspension of 1.5 g of 2-amino-4,6-dimethoxypyrimidine in 10 ml of methylene chloride. The product was soluble in the warm solution; however, a solid suspension resulted upon cooling to room temperature. The suspension was stirred overnight, then filtered and washed with 1-chlorobutane to yield 3.2 g of white solid, m.p. 153°–155° C. The infrared spectrum showed characteristic absorption bands at 3150 cm$^{-1}$, 1700 cm$^{-1}$, 1610 cm$^{-1}$, 1575 cm$^{-1}$.

By using molar equivalent amounts of an appropriate 2-aminopyrimidine and an appropriately substituted phenoxysulfonyl isocyanate, the compounds of Formula I set forth in Table I can be prepared by the procedure of Example 1.

TABLE I-A

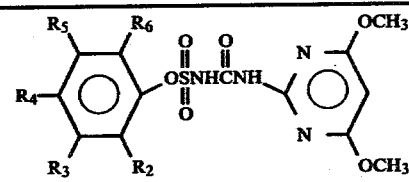

| $R_2$ | $R_3$ | $R_4$ | $R_5$ | $R_6$ | m.p. |
|---|---|---|---|---|---|
| H | H | H | H | H | 136–139 |
| Cl | H | H | H | H | 143–146 |
| Br | H | H | H | H | 153–155 |
| F | H | H | H | H | 146–148 |
| OCH$_3$ | H | H | H | H | 162–164 |
| CH(CH$_3$)$_2$ | H | H | H | H | 120–122 |
| Cl | H | Cl | H | H | 160–163 |
| Cl | H | H | Cl | H | 148–151 |
| Cl | H | Cl | H | Cl | 161–163 |
| H | Cl | Cl | H | H | 150–152 |
| Cl | Cl | H | H | H | 136–140 |
| OCH$_3$ | H | H | H | OCH$_3$ | 177–179 |
| CH$_3$ | H | H | H | CH$_3$ | 188–190 |
| Cl | H | H | H | Cl | 167–169 |
| C(CH$_3$)$_3$ | H | H | H | C(CH$_3$)$_3$ | 135–139 |
| CH(CH$_3$)$_2$ | H | H | H | CH(CH$_3$)$_2$ | 187–189 |
| CH$_3$ | H | H | H | C(CH$_3$)$_3$ | 150–153 |
| H | H | NO$_2$ | H | H | 170–171 |
| OCOCH$_3$ | H | H | H | H | 143–146 |
| H | H | CN | H | H | 154–157 |
| Cl | Cl | Cl | Cl | Cl | 164 |
| H | H | Cl | H | H | 152–154 |
| H | Cl | H | H | H | 130–132 |
| H | H | H | NO$_2$ | H | 115–119 |
| NO$_2$ | H | H | H | H | 153–154 |
| CF$_3$ | H | H | H | H | |
| H | OCH$_2$CH$_3$ | H | H | H | |
| H | H | (CH$_2$)$_3$CH$_3$ | H | H | |

TABLE I-A-continued

R5, R6 positions on phenyl; structure: R4-phenyl(R3,R2)-OSO2NHC(O)NH-pyrimidine(4,6-di-OCH3)

| R2 | R3 | R4 | R5 | R6 | m.p. |
|---|---|---|---|---|---|
| H | Br | H | H | H | |
| H | F | H | H | H | |
| H | H | O(CH2)3CH3 | H | H | 108–110 |
| H | H | H | CF3 | H | 103–105 |
| H | H | CONa (O=C) | H | H | |
| H | H | COH (O=C) | H | H | |
| H | H | CO(CH2)3CH3 (O=C) | H | H | |
| H | H | H | F | H | |
| H | H | H | Br | H | |
| H | H | H | CH3 | H | |
| H | H | H | H | Br | |
| H | H | H | H | F | |
| H | H | H | H | O(CH2)3CH3 | |
| CO(CH2)3CH3 (O=C) | H | H | H | H | 69–73 |
| —CH2CH3 | H | H | H | H | 68–72 |
| H | Cl | H | Cl | H | 174–175 |
| COCH3 (O=C) | H | H | H | CH3 | 137–139 |
| Br | H | CN | H | Br | 158–161 |
| H | H | COCH3 (O=C) | H | H | |
| NO2 | H | H | H | Cl | |
| O(CH2)3CH3 | H | H | H | H | |
| CONa (O=C) | H | H | H | H | |
| COH (O=C) | H | H | H | H | |
| H | H | CH3 | H | H | |
| H | OCH3 | H | H | H | |
| H | O(CH2)3CH3 | H | H | H | |

TABLE I-B

Structure: R4-phenyl(R3,R2,R5,R6)-OSO2NHC(O)NH-pyrimidine(4-OCH3, 6-CH3)

| R2 | R3 | R4 | R5 | R6 | m.p. |
|---|---|---|---|---|---|
| Cl | H | H | Cl | H | 170–172 |
| Cl | H | H | H | H | 138–141 |
| Cl | H | Cl | H | H | |
| Br | H | H | H | H | 143–145 |
| H | H | H | H | H | 155–157 |
| F | H | H | H | H | |
| NO2 | H | H | H | H | 150–151 |
| CH2CH3 | H | H | H | H | |
| OCH3 | H | H | H | H | |
| CF3 | H | H | H | H | |
| COCH3 (O=C) | H | H | H | H | 106–110 |
| H | Cl | H | H | H | |
| H | H | H | NO2 | H | |
| H | Br | H | H | H | |

TABLE I-B-continued

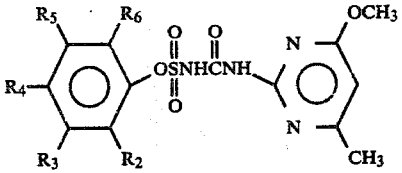

| R₂ | R₃ | R₄ | R₅ | R₆ | m.p. |
|---|---|---|---|---|---|
| H | F | H | H | H | |
| H | OCH₂CH₃ | H | H | H | |
| H | H | Cl | H | H | |
| H | H | Br | H | H | |
| H | H | F | H | H | |
| H | H | NO₂ | H | H | |
| H | H | CH₂CH₃ | H | H | |
| H | H | OCH₂CH₃ | H | H | |
| H | H | CN | H | H | |
| H | H | COCH₃ | H | H | |
| H | H | H | NO₂ | H | |
| H | H | H | CF₃ | H | |
| Cl | H | H | H | Cl | |
| CH(CH₃)₂ | H | H | H | CH(CH₃)₂ | |
| CH₃ | H | H | H | CH₃ | |
| H | H | O(CH₂)₃CH₃ | H | H | |
| Cl | H | H | OCH₃ | H | 75–78 |
| CHCH₂CH₃<br>\|<br>CH₃ | H | H | H | H | 150–152 |
| H | Cl | H | Cl | H | 173–175 |
| COCH₃ | H | H | H | CH₃ | 138–140 |
| Br | H | CN | H | Br | |
| H | H | (CH₂)₃CH₃ | H | H | |
| NO₂ | H | H | H | Cl | |

TABLE I-C

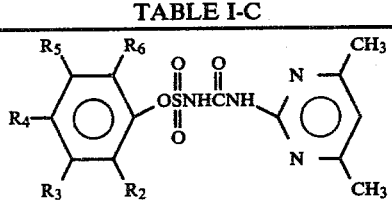

| R₂ | R₃ | R₄ | R₅ | R₆ | m.p. |
|---|---|---|---|---|---|
| Cl | H | Cl | H | H | 148–152 |
| H | H | H | H | H | 132–134 |
| Cl | H | H | H | H | |
| Br | H | H | H | H | 117–120 |
| F | H | H | H | H | |
| OCH₃ | H | H | H | H | |
| CH₃ | H | H | H | CH₃ | |
| CH(CH₃)₂ | H | H | H | H | |
| Cl | H | Cl | H | H | |
| Cl | H | H | Cl | H | |
| Cl | H | Cl | H | Cl | |
| H | Cl | Cl | H | H | |
| Cl | Cl | H | H | H | |
| OCH₃ | H | H | H | OCH₃ | |
| Cl | H | H | H | Cl | |
| H | H | NO₂ | H | H | |
| COCH₃ | H | H | H | H | |
| H | H | CN | H | H | |
| Cl | Cl | Cl | Cl | Cl | |
| H | H | H | NO₂ | H | |
| NO₂ | H | H | H | H | 95–100 |
| CF₃ | H | H | H | H | |
| H | OCH₂CH₃ | H | H | H | |
| H | Br | H | H | H | |
| H | F | H | H | H | |
| H | CH₃ | H | H | H | |

TABLE I-C-continued

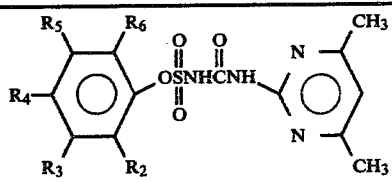

| R₂ | R₃ | R₄ | R₅ | R₆ | m.p. |
|---|---|---|---|---|---|
| H | H | F | H | H | |
| H | H | Br | H | H | |
| H | H | CH₂CH₃ | H | H | |
| H | H | OCH₃ | H | H | |
| H | H | CN | H | H | |
| H | H | CO₂CH₃ | H | H | |
| H | H | H | NO₂ | H | |
| H | H | H | CF₃ | H | |
| Br | H | CN | H | Br | |
| H | H | (CH₂)₃CH₃ | H | H | |
| NO₂ | H | H | H | Cl | |

TABLE I-D

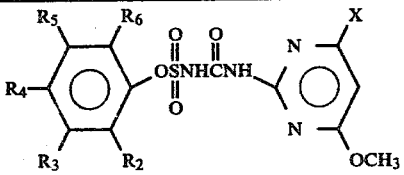

| R₂ | R₃ | R₄ | R₅ | R₆ | X |
|---|---|---|---|---|---|
| Cl | H | H | H | H | OCH₂CH₂OCH₃ |
| Cl | H | H | H | H | OCH₂CH₃ |

TABLE I-D-continued

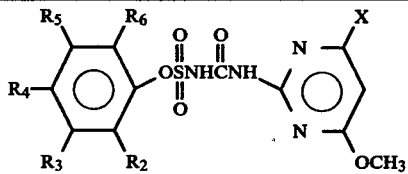

| R2 | R3 | R4 | R5 | R6 | X |
|---|---|---|---|---|---|
| CH3 | H | H | H | H | CH2OCH3 |
| Cl | H | H | H | H | SCH3 |
| Cl | H | H | H | H | CF3 |
| CH3 | H | H | H | H | SCH2CH3 |
| Cl | H | H | H | H | CH2CH3 |
| Cl | H | H | H | H | OCH2CH2CH3 |

TABLE I-E

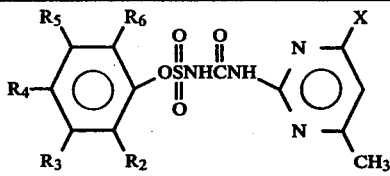

| R2 | R3 | R4 | R5 | R6 | X | m.p. |
|---|---|---|---|---|---|---|
| Cl | H | H | H | H | Cl | 116–119 |
| Cl | H | H | H | H | SCH3 | |
| CH3 | H | H | H | H | SCH2CH3 | |
| CH3 | H | H | H | H | CH2CH3 | |
| Cl | H | H | H | H | OCH2CH3 | |
| CH3 | H | H | H | H | OCH2CH2OCH3 | |

TABLE I-F

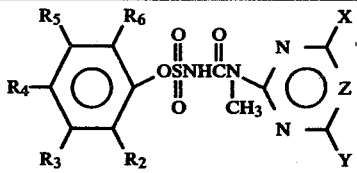

| R2 | R3 | R4 | R5 | R6 | X | Y | Z | m.p. |
|---|---|---|---|---|---|---|---|---|
| Cl | H | H | H | H | CH3 | CH3 | CH | |
| Cl | H | H | H | H | OCH3 | CH3 | CH | |
| CH3 | H | H | H | H | OCH3 | OCH3 | CH | |
| CH3 | H | H | H | H | CH3 | CH3 | N | |
| Cl | H | H | H | H | CH3 | OCH3 | N | |
| Cl | H | H | H | H | OCH3 | OCH3 | N | |
| H | H | H | H | H | OCH3 | OCH3 | N | 98–108 |

TABLE I-G

| R2 | R3 | R4 | R5 | R6 | X | Y | Z | m.p. |
|---|---|---|---|---|---|---|---|---|
| Cl | H | H | H | H | CH3 | CH3 | CH | |
| Cl | H | H | H | H | OCH3 | CH3 | CH | |
| CH3 | H | H | H | H | OCH3 | OCH3 | CH | |
| CH3 | H | H | H | H | CH3 | CH3 | N | |
| Cl | H | H | H | H | CH3 | OCH3 | N | |
| Cl | H | H | H | H | OCH3 | OCH3 | N | |

TABLE I-H

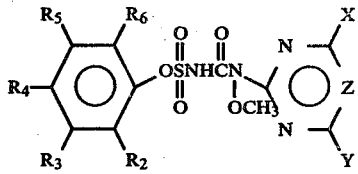

| R2 | R3 | R4 | R5 | R6 | X | Y | Z | m.p. |
|---|---|---|---|---|---|---|---|---|
| Cl | H | H | H | H | CH3 | CH3 | CH | |
| Cl | H | H | H | H | OCH3 | CH3 | CH | |
| CH3 | H | H | H | H | OCH3 | OCH3 | CH | |
| CH3 | H | H | H | H | CH3 | CH3 | N | |
| Cl | H | H | H | H | CH3 | OCH3 | N | |
| Cl | H | H | H | H | OCH3 | OCH3 | N | |

EXAMPLE 3

2,5-dichlorophenyl[4,6-dimethoxy-1,3,5-triazin-2-yl)-aminocarbonyl]sulfamate ester

To a well stirred solution of 1.6 g chlorosulfonyl isocyanate in 7 ml of dry xylene at ambient temperature and pressure was added 1.6 g of 2,5-dichlorophenol. The resulting mixture was heated to reflux temperature for 2 hours. The solvent was removed under reduced pressure to give a clear oil. The oil was diluted with 5 ml of methylene chloride and added to a cooled (ice-water bath) suspension of 1.5 g of 2-amino-4,6-dimethoxytriazine in 10 ml of methylene chloride. The mixture was stirred at room temperature for 16 hours, triturated with 1-chlorobutane and filtered to yield: 2.1 g of a tan solid, m.p. 139°–141° C. The infrared spectrum showed absorption bands at 3100 cm$^{-1}$, 1690 cm$^{-1}$, 1580 cm$^{-1}$, 1520 cm$^{-1}$.

By using an equivalent amount of the appropriate aminotriazine and an appropriately substituted phenoxysulfonyl isocyanate, the compounds given in Table II can be prepared by the procedure of Example 3.

TABLE II-A

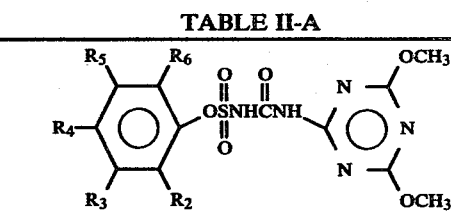

| R2 | R3 | R4 | R5 | R6 | m.p. |
|---|---|---|---|---|---|
| Cl | H | H | Cl | H | 139–141 |
| Br | H | H | H | H | |
| H | H | H | H | H | 160–161 |
| F | H | H | H | H | |
| OCH3 | H | H | H | H | |
| H | H | H | Cl | H | |
| H | H | Cl | H | H | |
| Cl | H | H | H | Cl | |
| CH3 | H | H | H | CH3 | |
| H | H | NO2 | H | H | |
| O‖COCH3 | | | | | |
| H | H | CN | H | H | |
| H | H | H | NO2 | H | |
| NO2 | H | H | H | H | |
| CF3 | H | H | H | H | |
| H | OCH2CH3 | H | H | H | |
| H | H | (CH2)3CH3 | H | H | |
| H | Br | H | H | H | |
| H | F | H | H | H | |
| H | CH3 | H | H | H | |
| H | H | Br | H | H | |

TABLE II-A-continued

[Structure: R4, R5, R6, R3, R2 substituted phenyl-OSNHCNH-pyrimidine with OCH3 groups at both positions]

| R2 | R3 | R4 | R5 | R6 | m.p. |
|---|---|---|---|---|---|
| H | H | F | H | H | |
| H | H | OCH3 | H | H | |
| H | H | OCOCH3 | H | H | |
| H | H | H | CF3 | H | |
| Br | H | CN | H | Br | |
| H | H | (CH2)3CH3 | H | H | |
| NO2 | H | H | H | Cl | |

TABLE II-B

[Structure: R4, R5, R6, R3, R2 substituted phenyl-OSNHCNH-pyrimidine with OCH3 and CH3]

| R2 | R3 | R4 | R5 | R6 | m.p. |
|---|---|---|---|---|---|
| H | H | H | H | H | 156–158 |
| Cl | H | H | H | H | 113–116 |
| Br | H | H | H | H | |
| F | H | H | H | H | |
| OCH3 | H | H | H | H | |
| H | H | Cl | H | H | |
| H | Cl | Cl | H | H | |
| CH3 | H | H | H | CH3 | |
| H | H | NO2 | H | H | |
| OCOCH3 | H | H | H | H | |
| H | H | CN | H | H | |
| H | H | H | NO2 | H | |
| NO2 | H | H | H | H | 80–85 |
| CF3 | H | H | H | H | |
| H | OCH2CH3 | H | H | H | |
| H | H | (CH2)3CH3 | H | H | |
| H | Br | H | H | H | |
| H | F | H | H | H | |
| H | CH3 | H | H | H | |
| H | H | Br | H | H | |
| H | H | F | H | H | |
| H | H | OCH3 | H | H | |
| H | H | OCOCH3 | H | H | |
| H | H | H | CF3 | H | |

TABLE II-C

[Structure: R4, R5, R6, R3, R2 substituted phenyl-OSNHCNH-pyrimidine with CH3 at both positions]

| R2 | R3 | R4 | R5 | R6 | m.p. |
|---|---|---|---|---|---|
| Cl | H | H | Cl | H | 107–110 |
| H | H | H | H | H | 138–141 |
| Cl | H | H | H | H | |
| Br | H | H | H | H | |
| F | H | H | H | H | |
| OCH3 | H | H | H | H | |
| H | H | Cl | H | H | |
| H | Cl | Cl | H | H | |
| CH3 | H | H | H | CH3 | |
| H | H | NO2 | H | H | |
| OCOCH3 | H | H | H | H | |
| H | H | CN | H | H | |
| H | H | H | NO2 | H | |
| NO2 | H | H | H | H | |
| CF3 | H | H | H | H | |
| H | OCH2CH3 | H | H | H | |
| H | H | (CH2)3CH3 | H | H | |
| H | Br | H | H | H | |
| H | F | H | H | H | |
| H | CH3 | H | H | H | |
| H | H | Br | H | H | |
| H | H | F | H | H | |
| H | H | OCH3 | H | H | |
| H | H | OCOCH3 | H | H | |

EXAMPLE 4

Sodium 2-{N-[(4,6-dimethoxypyrimidin-2-yl)aminocarbonyl]aminosulfonyloxy}benzoate To a well stirred solution of 0.5 g of methyl 2-{N-[(4,6-dimethoxypyrimidin-2-yl)aminocarbonyl]aminosulfonyloxy}benzoate in 15 ml of 95% ethanol was added 40 mg of sodium hydroxide, and the reaction mixture was heated to reflux temperature and stirred for two hours. The solvent was evaporated under reduced pressure to give the title sodium salt compound as a tan powder.

The sodium salt was dissolved in 20 ml of water and washed with 15 ml of ether. The aqueous phase was separated, acidified to pH of about 1 with conc. H2SO4. The mixture was then extracted with methylene chloride and dried (MgSO4). The solvent was removed under reduced pressure to give 0.3 g of a clear colorless glass. The infrared spectrum bands therefor showed characteristic absorption bands at 3400–2700 cm$^{-1}$ (broad), 1700 cm$^{-1}$ (broad).

Formulations

Useful formulations of the compounds of Formula I can be prepared in conventional ways. They include dusts, granules, pellets, suspensions, emulsions, wettable powders, emulsifiable concentrates and the like. Many of such formulations may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0% to 20% surfactant(s) or (b) about 1% to 99.9% solid or liquid diluent(s). More specifically, they will contain these ingredients in the approximate proportions set forth in Table III.

TABLE III

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions (including Emulsifiable Concentrates) | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active Ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual," MC Publishing Corp., Ridgewood, N.J., as well as Sisely and Wood, "Encyclopedia of Surface Active Agents," Chemical Publishing Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," *Chemical Engineering,* Dec. 4, 1967, pp. 147ff. and "Perry's Chemical Engineer's Handbook," 4th Ed., McGraw-Hill, New York, 1963, pp. 8–59ff.

For further information regarding the art of formulation, see example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, line 66 through Col. 5, line 17 and Examples 1–4.

G. C. Klingman, "Weed Control as a Science," John Wiley & Sons, Inc., New York, 1961, pp. 81–96.

J. D. Fryer and S. A. Evans, "Weed Control Handbook," 5th Ed., Blackwell Scientific Publications, Oxford, 1968, pp. 101–103.

In the following examples, all parts are by weight unless otherwise indicated.

EXAMPLE 5

| Wettable Powder | |
|---|---|
| 2,6-dimethylphenyl[(4-methoxy-6-methylpyrimidin-2-yl)-aminocarbonyl]sulfamate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until almost all of the solid particles thereof are under 50 microns in size, and then the ingredients are reblended.

EXAMPLE 6

| Wettable Powder | |
|---|---|
| 2,6-dimethoxyphenyl[(4-methoxy-6-methylpyrimidin-2-yl)-aminocarbonyl]sulfamate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active ingredient, almost all of which are below 10 microns in diameter. The product is reblended before packaging.

EXAMPLE 7

| Granule | |
|---|---|
| wettable powder of Example 6 | 5% |
| attapulgite granules (U.S.S. 20–40 mesh; 0.84–0.42 mm) | 95% |

A slurry of wettable powder containing about 25% solids is sprayed on the surface of attapulgite granules in a double-cone blender. The granules are dried and packaged.

EXAMPLE 8

| | |
|---|---|
| 2,6-dichlorophenyl[(4-methoxy-6-methylpyrimidin-2-yl)-aminocarbonyl]sulfamate | 25% |
| anhydrous sodium sulfate | 10% |
| crude calcium ligninsulfonate | 5% |
| sodium alkylnapthalenesulfonate | 1% |
| calcium/magnesium bentonite | 59% |

The ingredients are blended, hammer-milled and then moistened with about 12% water. The mixture is extruded as cylinders about 3 mm in diameter which are cut to produce pellets about 3 mm long. The pellets may be used directly after drying, or the dried pellets may be crushed to pass a U.S.S. No. 20 sieve (0.84 mm openings). Granules which can be held on a U.S.S. No. 40 sieve (0.42 mm openings) may be packaged for use and the fines recycled.

EXAMPLE 9

| Oil Suspension | |
|---|---|
| 2-chlorophenyl[(4-methoxy-6-methylpyrimidin-2-yl)-aminocarbonyl]sulfamate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns in size. The resulting suspension may be applied directly, but preferably after being extended with oils or emulsified in water.

EXAMPLE 10

| Wettable Powder | |
|---|---|
| 2,6-dimethylphenyl[(4-methoxy-6-methylpyrimidin-2-yl)-aminocarbonyl]sulfamate | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer mill to produce particles almost all of which are below 100 microns in size, the material is reblended and sifted through a U.S.S. No. 50 sieve (0.3 mm opening) and packaged.

EXAMPLE 11

| Low Strength Granule | |
|---|---|
| 2-chlorophenyl[(4-methoxy-6-methylpyrimidin-2-yl)-aminocarbonyl]sulfamate | 1% |
| N,N-dimethylformamide | 9% |
| attapulgite granules (U.S.S. 20–40 mesh) | 90% |

The active ingredient is dissolved in the solvent and the solution is sprayed upon dedusted attapulgite granules in a double cone blender. After spraying of the solution has been completed, the blender is allowed to run for a short period and then the granules are packaged.

EXAMPLE 12

| Aqueous Suspension | |
|---|---|
| phenyl[(4,6-dimethoxypyrimidine-2-yl)-aminocarbonyl]sulfamate | 40% |
| polyacrylic acid thickener | 0.3% |
| dodecylphenol polyethylene glycol ether | 0.5% |
| disodium phosphate | 1% |
| Monosodium phosphate | 0.5% |
| Polyvinyl alcohol | 1.0% |
| Water | 56.7% |

The ingredients are blended and ground together in a sand mill to produce particles almost all of which are under 5 microns in size.

EXAMPLE 13

| Low Strength Granule | |
|---|---|
| 2-chlorophenyl[(4-methoxy-6-methylpyrimidin-2-yl)-aminocarbonyl]sulfamate | 0.1% |
| attapulgite granules (U.S.S. 20–40 mesh) | 99.9% |

The active ingredient is dissolved in a solvent and the solution is sprayed upon dedusted attapulgite granules in a double cone blender. After spraying of the solution has been completed, the material is warmed to evaporate the solvent. The material is allowed to cool and then packaged.

EXAMPLE 14

| Granule | |
|---|---|
| 2,6-dimethoxyphenyl[(4-methoxy-6-methylpyrimidin-2-yl)-aminocarbonyl]sulfamate | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 15

| High Strength Concentrate | |
|---|---|
| phenyl[(4,6-dimethoxypyrimidin-2-yl)-aminocarbonyl]sulfamate | 99% |
| silica aerogel | 0.5% |
| synthetic amorphous silica | 0.5% |

The ingredients are blended and ground in a hammer-mill to produce a material almost all of which passes a U.S.S. No. 50 screen (0.3 mm opening). The concentrate may be formulated further if necessary.

EXAMPLE 16

| Wettable Powder | |
|---|---|
| 2,6-dimethylphenyl[(4-methoxy-6-methylpyrimidin-2-yl)-aminocarbonyl]sulfamate | 90% |
| dioctyl sodium sulfosuccinate | 0.1% |
| synthetic fine silica | 9.9% |

The ingredients are blended and ground in a hammermill to produce particles almost all of which are below 100 microns in size. The material is sifted through a U.S.S. No. 50 screen and then packaged.

EXAMPLE 17

| Wettable Powder | |
|---|---|
| 2,6-dichlorophenyl[(4-methoxy-6-methylpyrimidin- | |

-continued

| Wettable Powder | |
|---|---|
| 2-yl)-aminocarbonyl]sulfamate | 40% |
| sodium ligninsulfonate | 20% |
| montmorillonite clay | 40% |

The ingredients are thoroughly blended, coarsely hammer-milled and then air-milled to produce particles almost all of which are below 10 microns in size. The material is reblended and then packaged.

EXAMPLE 18

| Oil Suspension | |
|---|---|
| phenyl[(4,6-dimethoxypyrimidin-2-yl)-amino-carbonyl]sulfamate | 35% |
| blend of polyalcohol carboxylic esters and oil soluble petroleum sulfonates | 6% |
| xylene | 59% |

The ingredients are combined and ground together in a sand mill to produce particles almost all of which are below 5 microns in size. The product can be used directly, extended with oils, or emulsified in water.

EXAMPLE 19

| Wettable Powder | |
|---|---|
| 2,6-dimethoxyphenyl[(4-methoxy-6-methylpyrimidin-2-yl)-aminocarbonyl]sulfamate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all of the solid particles are thereof under 50 microns in size, reblended, and packaged.

EXAMPLE 20

| Wettable Powder | |
|---|---|
| 2,6-dichlorophenyl[(4-methoxy-6-methylpyrimidin-2-yl)-aminocarbonyl]sulfamate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles almost all of which are below 10 microns in diameter. The product is reblended before packaging.

EXAMPLE 21

| Granule | |
|---|---|
| Wettable powder of Example 20 | 5% |
| attapulgite granules (U.S.S. 20–40 mesh; 0.84–0.42 mm) | 95% |

A slurry of wettable powder containing about 25% solids is sprayed on the surface of attapulgite granules in a double-cone blender. The granules are dried and packaged.

EXAMPLE 22

| Extruded Pellet | |
|---|---|
| 2,6-dichlorophenyl[(4-methoxy-6-methylpyrimidine-2-yl)-aminocarbonyl]sulfamate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm in diameter which are cut to produce pellets about 3 mm long. The pellets may be used directly after drying, or the dried pellets may be crushed to pass a U.S.S. No. 20 sieve (0.84 mm openings). Granules which can be held on a U.S.S. No. 40 sieve (0.42 mm openings) may be packaged for use and the fines recycled.

EXAMPLE 23

| Oil Suspension | |
|---|---|
| 2-chlorophenyl[(4-methoxy-6-methylpyrimidin-2-yl)-aminocarbonyl]sulfamate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns in size. The resulting suspension may be applied directly, but preferably after being extended with oils or emulsified in water.

EXAMPLE 24

| Wettable Powder | |
|---|---|
| 2,6-dimethoxyphenyl[(4-methoxy-6-methylpyrimidin-2-yl)-aminocarbonyl]sulfamate | 20% |
| sodium alkylnapthalenesulfonate | 4% |
| sodium ligninsulfonate | 4% |
| low viscosity methyl cellulose | 3% |
| attapulgite | 69% |

The ingredients are thoroughly blended. After grinding in a hammer mill to produce particles almost all of which are below 100 microns in size, the material is reblended and sifted through a U.S.S. No. 50 sieve (0.3 mm opening) and packaged.

EXAMPLE 25

| Oil Suspension | |
|---|---|
| phenyl[(4,6-dimethoxypyrimidin-2-yl)-amino-carbonyl]sulfamate | 35% |
| blend of polyalcohol carboxylic esters and oil soluble petroleum sulfonates | 6% |
| xylene | 59% |

The ingredients are combined and ground together in a sand mill to produce particles almost all of which are below 3 microns in size. The product can be used directly, extended with oils, or emulsified in water.

EXAMPLE 26

| High Strength Concentrate | |
|---|---|
| 2,6-dimethylphenyl[(4-methoxy-6-methylpyrimidin-2-yl)-aminocarbonyl]sulfamate | 99% |
| silica aerogel | 0.5% |
| synthetic amorphous silica | 0.5% |

The ingredients are blended and ground in a hammer mill to produce a material almost all of which passes a U.S.S. No. 50 screen (0.3 mm opening). The concentrate may be formulated further if necessary.

EXAMPLE 27

| Low Strength Granule | |
|---|---|
| phenyl[(4,6-dimethoxypyrimidin-2-yl)-aminocarbonyl]sulfamate | 1% |
| N,N-dimethylformamide | 9% |
| attapulgite granules (U.S.S. 20–40 mesh) | 90% |

The active ingredient is dissolved in the solvent and the solution is sprayed upon dedusted attapulgite granules in a rotating blender. After spraying of the solution has been completed, the blender is allowed to run for a short period and then the granules are packaged.

EXAMPLE 28

| Aqueous Suspension | |
|---|---|
| 2-chlorophenyl[(4-methoxy-6-methylpyrimidin-2-yl)-aminocarbonyl]sulfamate | 40% |
| Polyacrylic acid thickener | 0.3% |
| Dodecylphenol polyethylene glycol ether | 0.5% |
| Disodium phosphate | 1% |
| Monosodium phosphate | 0.5% |
| Polyvinyl alcohol | 1.0% |
| Water | 56.7% |

The ingredients are blended and ground together in a sand mill to produce particles almost all of which are under 5 microns in size.

EXAMPLE 29

| Granule | |
|---|---|
| 2,6-dichlorophenyl[(4-methoxy-6-methylpyrimidin-2-yl)-aminocarbonyl]sulfamate | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 30

| Low Strength Granule | |
|---|---|
| 2,6-dimethoxyphenyl[(4-methoxy-6-methylpyrimidin-2-yl)-aminocarbonyl]sulfamate | 0.1% |
| attapulgite granules (U.S.S. 20–40 mesh) | 99.9% |

The active ingredient is dissolved in a solvent and the solution is sprayed upon dedusted attapulgite granules in a double-cone blender. After spraying of the solution has been completed, the material is warmed to evaporate the solvent. The material is allowed to cool and then packaged.

EXAMPLE 31

| Wettable Powder | |
|---|---|
| 2,6-dimethylphenyl[(4-methoxy-6-methylpyrimidin-2-yl)-aminocarbonyl]sulfamate | 90% |
| dioctyl sodium sulfosuccinate | 0.1% |
| synthetic fine silica | 9.9% |

The ingredients are blended and ground in a hammer mill to produce particles almost all of which are below 100 microns in size. The material is sifted through a U.S.S. No. 50 screen and then packaged.

UTILITY

The compounds of this invention are useful for the control of unwanted vegetation. They are particularly effective in controlling unwanted dicotyledonous plants (weeds) and may be used to remove such unwanted plants from monocotyledonous crops, such as rice and wheat. Application may be made either pre- or post-emergence, depending on the weeds to be controlled and the crop to be treated. Because of the variation possible in the crop, the compound to be used, soils, weather, etc., no one rate can be selected. The beneficial rates are in the range between 0.01 and 10 kg/ha, with a preferred range of 0.1 to 5 kg/ha. The lower rates are used for selective weed control on light soils or are applied to tender young plants. Higher rates may be used to control unwanted established plants in situations wherein no useful crop is involved.

The compounds of this invention may also be applied as directed sprays in established crops.

Ratings for compounds tested by Procedures A through C described hereinbelow are:

0 = no effect
& or 10 = maximum effect
B = burn
C = chlorosis or necrosis
D = defoliation
E = emergence inhibition
G = growth retardation
U = unusual pigmentation
6F = delayed flowering
6Y = abscised buds or flowers

TEST PROCEDURE A

Seeds of crabgrass (*Digitaria spp.*), barnyardgrass (*Echinochloa crusgalli*), wild oats (*Avena fatua*), cassia (*Cassia tora*), morningglory (*Ipomoea spp.*), cocklebur (*Xanthium spp.*), sorghum, corn, soybean, rice, wheat and nutsedge tubers were planted in a growth medium and treated preemergence with a nonphytotoxic solvent solution of the compounds set forth in Table IV. Other batches of seeds and tubers for all of the foregoing weed and crop plants were planted at the same time as controls. These control plantings were untreated; i.e., neither any compound nor any solvent was applied. At the same time, cotton having five leaves (including cotyledonary ones), bush beans with the second trifoliate leaf expanding, crabgrass with two leaves, barnyardgrass with two leaves, wild oats with one leaf, cassia with three leaves (including cotyledonary ones) morningglory with four leaves (including the cotyledonary ones), cocklebur with four leaves (including the cotyledonary ones), sorghum with three leaves, corn with three leaves, soybean with two cotyledonary leaves, rice with two leaves, wheat with two leaves, and nutsedge with three-five leaves were sprayed with a nonphytotoxic solvent solution of the compounds set forth in Table IV. Other groups of all of the same weed and crop plants were sprayed with the same nonphytotoxic solvent so as to provide control plants. Preemergence and postemergence treated plants and controls were maintained in a greenhouse for sixteen days, then all treated plants were compared with their respective controls and visually rated for response to treatment.

Ratings for tested compounds are recorded in Table IV. The data therein demonstrate the beneficial utility of compounds of this invention.

TABLE IV $$ROSNHCNH-\underset{\underset{Y}{N}}{\overset{\overset{X}{N}}{\bigcirc}}$$
(with S as SO$_2$ and C=O groups in the linker)

| R | ![3-Cl,2-CH3 phenyl] | ![2,6-diCl phenyl] | ![2,4-diCl phenyl] | ![2-CH3CHCH3 phenyl] | ![2-Cl phenyl] | ![2-Cl,6-CH3 phenyl] | ![2-C(CH3)3,6-CH3 phenyl] | ![2,6-di-CH(CH3)2 phenyl] | ![2,6-di-C(CH3)3 phenyl] | ![2,6-diCl phenyl] | ![2-OCH3 phenyl] |
|---|---|---|---|---|---|---|---|---|---|---|---|
| X | CH$_3$O | CH$_3$O | CH$_3$O | CH$_3$O | CH$_3$O | CH$_3$ | CH$_3$O | CH$_3$O | CH$_3$O | CH$_3$O | CH$_3$O |
| Y | CH$_3$ | CH$_3$O | CH$_3$O | CH$_3$O | CH$_3$O | CH$_3$ | CH$_3$O | CH$_3$O | CH$_3$O | CH$_3$O | CH$_3$O |
| Z | CH | CH | CH | CH | CH | CH | CH | CH | CH | CH | CH |
| kg/ha | 2 | 2 | 2 | 2 | 2 | 2 | 2 | 2 | 2 | 2 | 2 |

POST-EMERGENCE

| | | | | | | | | | | | |
|---|---|---|---|---|---|---|---|---|---|---|---|
| BUSH BEAN | — | — | 2C,3H,6F | 3H,8G,6Y | 9C | 1C,2H | 3C,3H,9G | 6C,9G | 3C,9G,6Y | 9C | 3C,4H,9G |
| COTTON | 3H | 1H | 3H | 2C,4H,9G | 9C | 1C | 3H,8G | 4C,8G | 2C,8G | 5C,8G | 9C |
| MORNING GLORY | 10C | 1B,9H | 10C | 9C | 10C | 1C,6G | 3C,9G | 10C | 3C,9G | 9C | 10C |
| COCKLEBUR | 9C | 6H | 9C | 9C | 9C | — | 3C,9G | 3H,9G | 3C,7G | 9C | 10C |
| CASSIA | 2C,7G | 3G | 6C | 5C,9G | 10C | 2G | 2C,5G | 2C,6G | 2C,6G | 10C | 9C |
| NUTSEDGE | 2C,8G | 2C,9G | 9G | 2C,8G | 9C | 3G | 4G | 1C,7G | 1C,7G | 4C,9G | 5C,8G |
| CRABGRASS | 1C,5G | 1C | 2G | 3G | 4G | 0 | 5G | 2C,6G | 0 | 2C,7G | 4G |
| BARNYARD GRASS | 1C | 2C | 1C | 3C,8H | 2C,6G | 0 | 1C,5G | 2C,6G | 1C,7G | 9H | 9H |
| WILD OATS | 0 | 0 | 0 | 0 | 2G | 0 | 0 | 0 | 0 | 2G | 0 |
| WHEAT | 0 | 0 | 0 | 0 | 0 | 0 | 2G | 1C | 0 | 1C,4G | 2G |
| CORN | 6G | 0 | 2G | 2C,9G | 5G | 1B,5G | 6H | 3C,9G | 0 | 6G | 7H |
| SOYBEAN | 5H | 2H,6G | 8C | 10C | 9C | 0 | 5G | 8G | 3C,8G | 5C,9G | 9C |
| RICE | 0 | 5G | 0 | 1C,6G | 5G | 0 | 5G | 0 | 8G | 7G | 1C,4G |
| SORGHUM | 7G | 0 | 2G | 2C,9G | 5G | 0 | 3G | 5G | 3G | 2C,9H | 1C,8G |

PRE-EMERGENCE

| | | | | | | | | | | | |
|---|---|---|---|---|---|---|---|---|---|---|---|
| MORNING GLORY | 9G | 9G | 9G | 10E | 9G | 9G | 9G | 9G | 9G | 10E | 10E |
| COCKLEBUR | 9G | 8G | 9G | 9G | 9G | 10E | 8G | 8G | 8G | 9G | 10E |
| CASSIA | 9G | 5G | 9G | 9C | 2C,9G | 2G | 7G | 9G | 7G | 9G | 9G |
| NUTSEDGE | 9G | 0 | 10E | 10E | 10E | 0 | 9G | 9G | 10E | 10E | 10E |
| CRABGRASS | 1C | 0 | 2G | 2C,8G | 1C,5G | 0 | 2C | 2C,6G | 3G | 1C,8G | 1C,9G |
| BARNYARD GRASS | 2C | 1C,6G | 4C | 4C,9H | 2C,8G | 0 | 2C,6G | 1G | 2C,8H | 9G | 1C,9G |
| WILD OATS | 3G | 0 | 1C | 4G | 1G | 0 | 0 | 4G | 2G | 6G | 4G |
| WHEAT | 2G | 0 | 0 | 5G | 2G | 2C | 3G | 3G | 3G | 9H | 4G |
| CORN | 9H | 1C,7G | 1C,7G | 3C,9H | 3H,9C | 0 | 2C,6G | 4G | 9G | 9G | 9H |
| SOYBEAN | 8H | 1C,3H | 8H | 10E | 9H | 0 | 9H | 2C,9G | 9H | 9H | 9H |
| RICE | 9G | 9H | 7G | 5C,9H | 9H | 6G | 8H | 8H | 9H | 9H | 2C,9H |
| SORGHUM | 2C | 2C | 2G | 3C,9G | 7C | 2G | 1C,7G | 9H | 3G | 2C,9G | 1C,9H |

TABLE IV-continued $$\text{ROSNHCNH-}\underset{\underset{O}{\|}}{\underset{O}{\|}}\text{-ring with X, Y, Z, N}$$

| R | | | | | | | | | | | | |
|---|---|---|---|---|---|---|---|---|---|---|---|---|
| | 2-Cl-4-CH₃-C₆H₃ | 3-Cl-5-CH₃-C₆H₃ | 2,6-Cl₂-4-CH₃-C₆H₂ | 2,4-Cl₂-C₆H₃ | 2-F-C₆H₄ | 2,6-(CH₃)₂-C₆H₃ | 2,6-(OCH₃)₂-C₆H₃ | 3-NO₂-C₆H₄ | 2,4-Cl₂-C₆H₃ | C₆H₅ | 2-Br-C₆H₄ | 3,4-Cl₂-C₆H₃ |
| X | CH₃O | CH₃ | CH₃O | CH₃O | CH₃O | CH₃O | CH₃O | CH₃O | CH₃O | CH₃O | CH₃O | CH₃O |
| Y | CH₃ | CH₃ | CH₃O | CH₃O | CH₃O | CH₃O | CH₃O | CH₃O | CH₃O | CH₃O | CH₃O | CH₃ |
| Z | CH | N | CH | CH | CH | CH | CH | CH | CH | CH | CH | CH |
| kg/ha | 2 | 2 | 2 | 2 | 2 | 2 | 2 | 2 | 2 | 2 | 2 | 2 |

POST-EMERGENCE

| | | | | | | | | | | | | |
|---|---|---|---|---|---|---|---|---|---|---|---|---|
| BUSH BEAN | 9C | 0 | 2C,9G,6Y | 4C,7G,6Y | 10C | 5C,9G,9D | 9C | 2C,8G,6Y | — | — | — | — |
| COTTON | 6C,9G | 1H | 1C,2H | 2C | 4C,9G | 5C,7G | 9C | 2C,5G | 1C | 4C,3H,9G | 6C,9G | 4H |
| MORNING GLORY | 10C | 2G | 1C | 2C,8G | 10C | 10C | 10C | 2C,8G | 0 | 10C | 10C | 10C |
| COCKLEBUR | 9C | 1C,3G | 1C | 5C,9G | 9C | 10C | 10C | 2C,9G | 1C | 10C | 10C | 9C |
| CASSIA | 9C | 3G | 1C | 2C | 9C | 9C | 9C | 1C,5G | 0 | 9C | 10C | 3C,8G |
| NUTSEDGE | 9G | 0 | 8G | 2C,8G | 7C,9G | 9G | 4C,9G | 1C,8G | 0 | 10C | 10C | 1C,7G |
| CRABGRASS | 7G | 0 | 2G | 0 | 6G | 7G | 1C,8G | 2C | 0 | 2C,9G | 2C,6G | 3G |
| BARNYARD GRASS | 2C,9H | 1C | 0 | 2C,8G | 5C,8H | 2C,9G | 9C | 2G | 0 | 3C,9H | 2C,7H | 2G |
| WILD OATS | 4G | 0 | 3G | 0 | 6G | 2G | 6G | 2G | 0 | 3G | 0 | 0 |
| WHEAT | 3G | 0 | 0 | 0 | 0 | 2G | 1C,8G | 0 | — | 2G | 0 | 0 |
| CORN | 9G | 3G | 3G | 2G | 1C,7G | 1C,7G | 5C,9G | 5G | 4G | 2H,8G | 2U,7G | 4G |
| SOYBEAN | 9H | 1G | 2H,9G | 1H,5G | 3C,9G | 6C,9G | 9C | 1C,7G | 1H | 4C,9G | 9C | 7H |
| RICE | 2C,9G | 0 | 3G | 0 | 1C,7G | 7G | 2C,9G | 4G | 0 | 6G | 3G | 0 |
| SORGHUM | 2C,9G | 5G | 2G | 2G | 8G | 8G | 1C,9G | 1C,9G | 0 | 1C,9G | 4G | 7G |

PRE-EMERGENCE

| | | | | | | | | | | | | |
|---|---|---|---|---|---|---|---|---|---|---|---|---|
| MORNING GLORY | 10E | — | 9C | 9G | 10E | 10E | 9G | 9G | 9G | 10E | 10E | 9G |
| COCKLEBUR | 9G | 0 | 9G | 9G | 10E | 10E | 9G | 9G | — | 9G | 9G | 9G |
| CASSIA | 10E | 0 | 7G | 9G | 5C,9G | 9C | 10C | 9C | 3G | 9C | 9C | 9C |
| NUTSEDGE | 10E | 0 | 8G | 10E | 10E | 10E | 10E | 10E | 0 | 10E | 10E | 1C,8G |
| CRABGRASS | 7G | 0 | 2G | 5C | 1C,8G | 9G | 1C,9G | 8G | 0 | 2C,7G | 2C,5G | 2C |
| BARNYARD GRASS | 9H | 0 | 2C,8H | 0 | 5C,9G | 1C,9G | 10C | 1C | 0 | 3C,9H | 2C,8G | 3C,8G |
| WILD OATS | 7G | 0 | 3G | 5C | 3G | 10C | 1C,9G | 2G | 0 | 3G | 2C | 1C |
| WHEAT | 8G | 0 | 5G | 0 | 5G | 4G | 2H,9G | 1C,9H | 0 | 3G | 5G | 3G |
| CORN | 9G | 2G | 1C,7G | 1C,5G | 1C,9G | 8G | 10E | 9H | 3G | 1C,9G | 1C,7G | 2C,8G |
| SOYBEAN | 9H | 0 | 4H | 5G | 9H | 9H | 10E | 9H | — | 9H | 9H | 9H |
| RICE | 9H | 0 | 9H | 1C,6G | 1C,9G | 9H | 10E | 9H | 6H | 9G | 9H | 8H |
| SORGHUM | 10C | 2G | 6G | 2G | 1C,9G | 3H,9G | 9H | 1C,9G | 0 | 1C,9G | 1C,7G | 2C,9G |

TEST PROCEDURE B

Two plastic bulb pans were filled with fertilized and limed Fallsington silt loam soil. One pan was planted with seeds of corn, sorghum and several grassy weeds. The other pan was planted with seeds of soybeans, purple nutsedge tubers (Cyperus rotundus), and seeds of several broadleaf weeds. Seeds of the following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), curly indigo (*Aeschynomene virginica*), morningglory (*Ipomoea hederacea*), cassia (*Cassia tora*), teaweed (*Sida spinosa*), velvetleaf (*Abutilon theophrasti*), and jimsonweed (*Datura stramonium*). A 5-inch diameter plastic pot was also filled with prepared soil and planted with rice and wheat seeds. Another 5-inch pot was planted with seeds of sugarbeets. The above four containers were treated preemergence with nonphytotoxic solvent solutions of the compounds set forth in Table V (i.e. solutions of said compounds sprayed on soil surface before seed germination). Duplicates of the above-described seeded containers were prepared without treatment and used as controls.

Twenty-eight days after treatment, the treated and control plants were evaluated and the data recorded as set forth in Table V. The results show the utility of these compounds for preemergence weed control in wheat and rice.

TABLE V

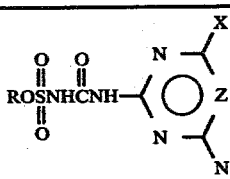

PRE-EMERGENCE HERBICIDE
Fallsington Silt Loam

| X | CH₃O |
| Y | CH₃O |
| Z | CH |

| Rate, kg/ha | 0.06 | 0.25 |
|---|---|---|
| Crabgrass | 0 | 0 |
| Barnyardgrass | 0 | 3G |
| Sorghum | 0 | 0 |
| Wild oats | 0 | 0 |
| Johnsongrass | 0 | 4G |
| Dallasgrass | 0 | 0 |
| Giant foxtail | 0 | 0 |
| Ky. bluegrass | 0 | 3G |
| Cheatgrass | 0 | 0 |
| Sugarbeets | 9C,9G | 10C |
| Corn | 0 | 2U,3G |
| Mustard | 9C,9G | 10C |
| Cocklebur | 4G | 6G |
| Pigweed | 10C | 10C |
| Nutsedge | 8G | 10E |
| H. indigo | — | — |
| Morningglory | 6G | 8G |
| Cassia | 6G | 8G,8C |
| Teaweed | 8G | 10C |

TABLE V-continued

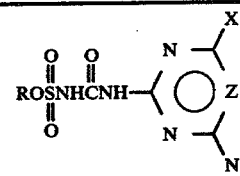

PRE-EMERGENCE HERBICIDE
Fallsington Silt Loam

| Velvetleaf | 9G | 10C |
|---|---|---|
| Jimsonweed | 7G | 8G,5C |
| Soybean | 3H | 8G,8H |
| Rice | 0 | 0 |
| Wheat | 0 | 0 |

TEST PROCEDURE C

Twenty-five cm - diameter plastic pots filled with Fallsington silt loam were planted to soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea* spp.), jimsonweed (*Datura stramonium*), cocklebur (*Xanthium pennsylvanicum*), crabgrass (*Digitaria* spp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with compounds of Table VI dissolved in a nonphytotoxic solvent. Other groups of all of the same weed and crop plants were sprayed with the same nonphytotoxic solvent so as to provide control plants. Fourteen days after treatment, all treated plants were compared with the nonphytotoxic solvent controls and visually rated for response to treatment to give the data presented in Table VI. These data illustrates the value of these compounds for selective postemergence control of broadleaves in rice, sorghum and wheat.

TABLE VI

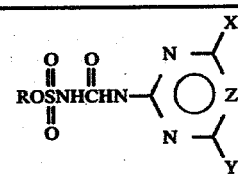

Over-the-Top Soil/Foliage Treatment

| X | CH₃O |
| Y | CH₃O |
| Z | CH |

| Rate, kg/ha | 0.06 | 0.25 |
|---|---|---|
| Soybeans | 10G,8C | 10C |
| Velvetleaf | 8G,6C | 10C |
| Sesbania | 10C | 10C |
| Cassia | 8G,5C | 10G,7C |
| Cotton | 10G,6C | 10C |
| Morningglory | 10C | 10C |
| Alfalfa | 10G,7C | 8G,5C |
| Jimsonweed | 10G,8C | 10G,7C |
| Cocklebur | 10G,9C | 10C |
| Corn | 3G | 3G |
| Crabgrass | 0 | 4G |
| Rice | 0 | 0 |

TABLE VI-continued

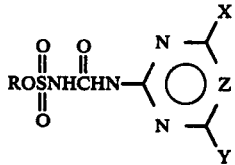

| Over-the-Top Soil/Foliage Treatment | | |
|---|---|---|
| Nutsedge | 4C | 4C |
| Barnyardgrass | 3G | 3G |
| Wheat | 0 | 4G |
| Giant Foxtail | 0 | 0 |
| Wild Oats | 0 | 0 |
| Sorghum | 0 | 0 |

What is claimed is:

1. A compound having the formula

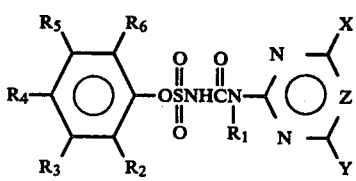

wherein
$R_1$ is H, $OCH_3$ or alkyl of 1–3 carbons;
$R_2$ is H, Cl, F, Br, $NO_2$, alkyl of 1–4 carbons, alkoxy of 1–4 carbons, $CF_3$ or

$R_3$ is H, Cl, F, Br, $CH_3$, or alkoxy of 1–4 carbons;
$R_4$ is H, Cl, F, Br, $NO_2$, alkyl of 1–4 carbons, alkoxy of 1–4 carbons, CN or

$R_5$ is H, Cl, F, Br, $CH_3$, $NO_2$ or $CF_3$;
$R_6$ is H, Cl, F, Br, alkyl of 1–4 carbons or alkoxy of 1–4 carbons;
$R_7$ is NaO, OH, or alkoxy of 1–4 carbons;
X is $CH_3$, $CH_3CH_2$, alkoxy of 1–3 carbons, $CH_3OCH_2$, $CH_3OCH_2CH_2O$, $CH_3S$, $CH_3CH_2S$, $CF_3$ or Cl; and
Y is $CH_3$, $CH_3CH_2$, alkoxy of 1–3 carbons, $CH_3OCH_2$, $CH_3OCH_2CH_2O$, $CH_3S$ or $CH_3CH_2S$;
Z is CH or N;
provided that
only one of $R_2$, $R_3$ or $R_4$ is alkoxy; and
when $R_5$ is $NO_2$, $R_4$ is other than $NO_2$.

2. A compound of claim 1 wherein $R_1$ is hydrogen.
3. A compound of claim 1 wherein X and Y are independently $CH_3$ or $CH_3O$.
4. A compound of claim 1 wherein
$R_2$ and $R_4$ are independently H, Cl, alkyl of 1–4 carbons, $CH_3O$ or

$R_3$ is H, Cl, $CH_3$ or $—OCH_3$;
$R_5$ is H, Cl, $CH_3$ or $NO_2$;
$R_6$ is H, Cl, alkyl of 1–4 carbons or $—OCH_3$; and
$R_7$ is $CH_3O$, or $CH_3CH_2O$.

5. A compound of claim 4 wherein $R_1$ is hydrogen.
6. A compound of claim 4 wherein X and Y are independently $CH_3$ or $CH_3O$.
7. A compound of claim 4 wherein $R_3$, $R_4$ and $R_5$ are H.
8. The compound of claim 1 which is phenyl[(4,6-dimethoxypyrimidin-2-yl)-aminocarbonyl]sulfamate.
9. The compound of claim 1 which is phenyl [(4,6-dimethoxy-1,3,5-triazin-2-yl)-aminocarbonyl]sulfamate.
10. The compound of claim 1 which is 2-chlorophenyl[(4-methoxy-6-methylpyrimidin-2-yl)-aminocarbonyl]sulfamate.
11. The compound of claim 1 which is 2,6-dichlorophenyl[(4-methoxy-6-methylpyrimidin-2-yl)-aminocarbonyl]sulfamate.
12. The compound of claim 1 which is 2,6-dimethoxyphenyl[(4-methoxy-6-methylpyrimidin-2-yl)-aminocarbonyl]sulfamate.
13. The compound of claim 1 which is 2,6-dimethylphenyl[(4-methoxy-6-methylpyrimidin-2-yl)-aminocarbonyl]sulfamate.
14. The compound of claim 1 which is methyl 2-{N-[(4-methoxy-6-methylpyrimidin-2yl)-aminocarbonyl]aminosulfonyloxy}benzoate.
15. The compound of claim 1 which is 2-nitrophenyl[(4,6-dimethoxypyrimidin-2-yl)-amino carbonyl]sulfamate.
16. The compound of claim 1 which is methyl 2-{N-[(4,6-dimethoxypyrimidin-2-yl)-aminocarbonyl]aminosulfonyloxy}-3-methylbenzoate.
17. A composition suitable for controlling the growth of undesired vegetation which comprises an herbicidally effective amount of a compound of claim 1 and at least one of the following: surfactant, solid or liquid diluent.
18. A composition suitable for controlling the growth of undesired vegetation which comprises an herbicidally effective amount of a compound of claim 2 and at least one of the following: surfactant, solid or liquid diluent.
19. A composition suitable for controlling the growth of undesired vegetation which comprises an herbicidally effective amount of a compound of claim 3 and at least one of the following: surfactant, solid or liquid diluent.
20. A composition suitable for controlling the growth of undesired vegetation which comprises an herbicidally effective amount of a compound of claim 4 and at least one of the following: surfactant, solid or liquid diluent.
21. A composition suitable for controlling the growth of undesired vegetation which comprises an herbicidally effective amount of a compound of claim 5 and at least one of the following: surfactant, solid or liquid diluent.
22. A composition suitable for controlling the growth of undesired vegetation which comprises an herbicidally effective amount of a compound of claim 6 and at least one of the following: surfactant, solid or liquid diluent.
23. A composition suitable for controlling the growth of undesired vegetation which comprises an herbicidally effective amount of a compound of claim 7 and at least one of the following: surfactant, solid or liquid diluent.

24. A composition suitable for controlling the growth of undesired vegetation which comprises an herbicidally effective amount of the compound of claim 8 and at least one of the following: surfactant, solid or liquid diluent.

25. A composition suitable for controlling the growth of undesired vegetation which comprises an herbicidally effective amount of the compound of claim 9 and at least one of the following: surfactant, solid or liquid diluent.

26. A composition suitable for controlling the growth of undesired vegetation which comprises an herbicidally effective amount of the compound of claim 10 and at least one of the following: surfactant, solid or liquid diluent.

27. A composition suitable for controlling the growth of undesired vegetation which comprises an herbicidally effective amount of the compound of claim 11 and at least one of the following: surfactant, solid or liquid diluent.

28. A composition suitable for controlling the growth of undesired vegetation which comprises an herbicidally effective amount of the compound of claim 12 and at least one of the following: surfactant, solid or liquid diluent.

29. A composition suitable for controlling the growth of undesired vegetation which comprises an herbicidally effective amount of the compound of claim 13 and at least one of the following: surfactant, solid or liquid diluent.

30. A composition suitable for controlling the growth of undesired vegetation which comprises an herbicidally effective amount of the compound of claim 14 and at least one of the following: surfactant, solid or liquid diluent.

31. A composition suitable for controlling the growth of undesired vegetation which comprises an herbicidally effective amount of the compound of claim 15 and at least one of the following: surfactant, solid or liquid diluent.

32. A composition suitable for controlling the growth of undesired vegetation which comprises an herbicidally effective amount of the compound of claim 16 and at least one of the following: surfactant, solid or liquid diluent.

33. A method for protecting against the growth of undesired vegetation which comprises applying to the locus to be protected an herbicidally effective amount of a compound of claim 1.

34. A method for protecting against the growth of undesired vegetation which comprises applying to the locus to be protected an herbicidally effective amount of a compound of claim 2.

35. A method for protecting against the growth of undesired vegetation which comprises applying to the locus to be protected an herbicidally effective amount of a compound of claim 3.

36. A method for protecting against the growth of undesired vegetation which comprises applying to the locus to be protected an herbicidally effective amount of a compound of claim 4.

37. A method for protecting against the growth of undesired vegetation which comprises applying to the locus to be protected an herbicidally effective amount of a compound of claim 5.

38. A method for protecting against the growth of undesired vegetation which comprises applying to the locus to be protected an herbicidally effective amount of a compound of claim 6.

39. A method for protecting against the growth of undesired vegetation which comprises applying to the locus to be protected an herbicidally effective amount of a compound of claim 7.

40. A method for protecting against the growth of undesired vegetation which comprises applying to the locus to be protected an herbicidally effective amount of the compound of claim 8.

41. A method for protecting against the growth of undesired vegetation which comprises applying to the locus to be protected an herbicidally effective amount of the compound of claim 9.

42. A method for protecting against the growth of undesired vegetation which comprises applying to the locus to be protected an herbicidally effective amount of the compound of claim 10.

43. A method for protecting against the growth of undesired vegetation which comprises applying to the locus to be protected an herbicidally effective amount of the compound of claim 11.

44. A method for protecting against the growth of undesired vegetation which comprises applying to the locus to be protected an herbicidally effective amount of the compound of claim 12.

45. A method for protecting against the growth of undesired vegetation which comprises applying to the locus to be protected an herbicidally effective amount of the compound of claim 13.

46. A method for protecting against the growth of undesired vegetation which comprises applying to the locus to be protected an herbicidally effective amount of the compound of claim 14.

47. A method for protecting against the growth of undesired vegetation which comprises applying to the locus to be protected an effective amount of the compound of claim 15.

48. A method for protecting against the growth of undesired vegetation which comprises applying to the locus to be protected an herbicidally effective amount of the compound of claim 16.

* * * * *